United States Patent
Tian

(10) Patent No.: US 11,259,555 B2
(45) Date of Patent: Mar. 1, 2022

(54) SPECIALIZED FLOUR FOR NUTRITION MEALS FOR DIABETES AND PREPARATION METHOD AND USE THEREOF

(71) Applicant: Jianhua Tian, Anyang (CN)

(72) Inventor: Jianhua Tian, Anyang (CN)

( * ) Notice: Subject to any disclaimer, the term of this patent is extended or adjusted under 35 U.S.C. 154(b) by 226 days.

(21) Appl. No.: 15/328,868

(22) PCT Filed: Aug. 3, 2015

(86) PCT No.: PCT/CN2015/085956
§ 371 (c)(1),
(2) Date: Apr. 26, 2017

(87) PCT Pub. No.: WO2016/015681
PCT Pub. Date: Feb. 4, 2016

(65) Prior Publication Data
US 2017/0224001 A1  Aug. 10, 2017

(30) Foreign Application Priority Data
Aug. 1, 2014  (CN) .......................... 201410380120.9

(51) Int. Cl.
| | |
|---|---|
| A23L 33/00 | (2016.01) |
| A23L 33/22 | (2016.01) |
| A21D 2/26 | (2006.01) |
| A21D 13/062 | (2017.01) |
| A23L 33/185 | (2016.01) |
| A23L 33/10 | (2016.01) |
| A21D 2/36 | (2006.01) |

(52) U.S. Cl.
CPC .............. *A23L 33/40* (2016.08); *A21D 2/266* (2013.01); *A21D 2/362* (2013.01); *A21D 13/062* (2013.01); *A23L 33/10* (2016.08); *A23L 33/185* (2016.08); *A23L 33/22* (2016.08); *A23V 2002/00* (2013.01); *A23V 2200/00* (2013.01); *A23V 2200/328* (2013.01); *A23V 2250/5116* (2013.01); *A23V 2250/5488* (2013.01)

(58) Field of Classification Search
None
See application file for complete search history.

(56) References Cited

FOREIGN PATENT DOCUMENTS

HU  0501123  *  1/2006

OTHER PUBLICATIONS

NutritionValue.Org, "Gums, seed gums (includes locust bean, guar)"—https://www.nutritionvalue.org, downloaded Oct. 12, 2018. (Year: 2018).*
NutritionValue.Org, "Soy flour, defatted"—https://www.nutritionvalue.org, downloaded Oct. 12, 2018. (Year: 2018).*
NutritionValue.Org, "Oat flour, partially debranned"—https://www.nutritionvalue.org, downloaded Oct. 12, 2018. (Year: 2018).*
NutritionValue.Org, "Wheat flour, enriched, bread, white"—https://www.nutritionvalue.org, downloaded Oct. 12, 2018. (Year: 2018).*
Nuttal, F., "Dietary Fiber in the Management of Diabetes", Diabetes, vol. 42, Apr. 1993, pp. 503-508. (Year: 1993).*
Gonzalez-Galan et al., "Sensory and Nutritional Properties of Cookies Based on Wheat—Rice—Soybean Flours Baked in a Microwave Oven"—Journal Food Science, vol. 56, No. 6, 1991, pp. 1699-1701. (Year: 1991).*
NutritionValue.Org—"Rice flour, unenriched, white"; https://www.nutritionvalue.org, downloaded Mar. 11, 2020. (Year: 2020).*
Kovacs (HU 0501123 A—English translation of application on IP.com ) (Year: 2007).*
European Patent Communication Under Rule 71(3) EPC for Related Patent Application No. 15827115.5, dated Jul. 12, 2019, 7 Pages.
European Patent Application Description for Related Patent Application No. 15827115.5, Dated Jul. 18, 2018, 40 Pages.

* cited by examiner

*Primary Examiner* — Elizabeth Gwartney
(74) *Attorney, Agent, or Firm* — Lewis Roca Rothgerber Christie LLP

(57) ABSTRACT

Disclosed are specialized flour for nutrition meals for diabetes and a preparation method and use thereof. The flour is based on cereal meal as a basic material and is added to a defatted soybean vegetable protein powder and a soybean tissue isolated dietary fiber power, wherein in the dry flour base, the content of protein is 20-26 weight %, the content of the dietary fiber is 4-10 weight %, the content of carbohydrate is no more than 65 weight %, and the content of fat is no more than 4% of the weight. The method comprises physically mixing the cereal meal, the defatted soybean vegetable protein powder and the soybean tissue isolated dietary fiber power under atmospheric pressure. Food and semi-finished products made from the flour are used for preventing and/or treating diabetes.

2 Claims, No Drawings

SPECIALIZED FLOUR FOR NUTRITION MEALS FOR DIABETES AND PREPARATION METHOD AND USE THEREOF

CROSS-REFERENCE TO RELATED APPLICATION(S)

This application is a National Phase Patent Application and claims priority to and the benefit of International Application Number PCT/CN2015/085956, filed on Aug. 3, 2015, which claims priority to Chinese Patent Application Number 201410380120.9, filed on Aug. 1, 2014, the entire contents of all of which are incorporated herein by reference.

TECHNICAL FIELD

The invention relates to the field of food raw materials and is mainly used for diabetic patients, particularly relates to a specialized flour for nutritional meals for diabetic patients and preparation method and use thereof.

BACKGROUND

Diabetes dietary management is a basic method for preventing and treating diseases and has been written to the guidelines for prevention and treatment of by countries around the world. Because excessive dietary energy and excessive fat are not only a single cause leading to obesity and the like, but also superpose all other causes to increase contributing conditions. Moreover, diabetic complications are not only caused by hyperglycemia, but also caused by common pathology of all types of diabetes, for example, glycometabolism disorders result in the decrease and delay of the output of the carbohydrate energy and the energy loss through urine, so the protein and fat are required to instead of carbohydrates to sustain life, as well as the energy generated by delayed decomposition of blood glucose cannot consume synthetic fat, so that the fat anabolism and catabolism are increased, the blood lipids are elevated and the blood vessels are blocked; the increased protein consumption. and the reduced repair capacity of immunity and tissues will cause series of complications. Such situation can be corrected by limiting when the foods or nutrition are too much or supplementing when the foods or nutrition are too little. Meanwhile, all hypoglycemic agents can only help the body to improve their own glucose metabolism deficiencies, they cannot be safely and effectively used as the digestion and absorption rate vary with the carbohydrates, the amount and accompanying ingredients from different foods, causing varied and fluctuant blood glucose levels.

Therefore although exercise, hypoglycemic agents and the like are indispensable for the prevention and treatment of diabetes, they should combine with the dietary management. Otherwise, not only the blood glucose would be definitely out of control and the treatment will lead to metabolic disorders and aggravate the causes and complications. Since there is no alternative nutrition to sustain life, the body can only passively use the blood glucose, but this will occupy other different paths and their bioavailability. For example, the blood glucose can be decomposed, but the amount of the blood glucose can not controlled, thus too much blood glucose will synthesize the fat. The carbohydrate absorption can be inhibited, the metabolism in the periphery can be promoted, and the energy consumption of exercise can be increased, the insufficient blood glucose will cause metabolism disorders, so that the body needs to call more lipoproteins, on one hand to convert lipoproteins into the blood glucose by gluconeogenesis, on the other hand to burn the lipoproteins directly to provide energy. Otherwise, not only the blood glucose cannot be maintained in a stable level, but also human basic life activities such as respiration, heartbeat, body temperature and the like cannot be normally performed. However, this process has the same pathology with diabetes and the complications thereof which are directly caused by diet.

That is to say, the diabetes dietary management is mainly divided into two aspects: one is to reduce the content of saturated fat, ensuring the comprehensive nutrition management goal characterized by the basic needs of carbohydrate foods such as protein and starch, the aim of doing so is to correct metabolic disorders by limiting when the foods or nutrition are too much or supplementing when the foods or nutrition are too little, thus naturally improving the working efficiency of insulin, improving the blood glucose and blood lipids, relieving the burden of pancreas islet, saving the hypoglycemic agents, and naturally reducing complications; and the other is to stabilize and control the different carbohydrate foods and different accompanying ingredients thereof which will influence the changes of blood glucose, thereby steadily reducing the postprandial blood glucose levels, the aim of doing so is as follows: on one hand, more blood glucose are naturally metabolized through the residual pancreatic function of the patients and exercise and the like, and the hypoglycemic agents are directly saved; on the other hand, the changes of blood glucose in the course of intaking are also stabilized thereby ensuring hypoglycemic agents can be used safely and effectively.

However, it is not easy to implement the above two targets. Because the foods is often not a single substance, different components will mutually influence during matching process, and vary with various factors such as different processing methods, different edible parts and the like. Moreover, the nutritional distribution of natural foods is not reasonable. For example, high-protein foods such as meat, egg and milk are rich in saturated fat, coarse grain and other high-dietary fiber foods are rich in high-density starch and other carbohydrates, the protein is small in amount and poor in quality. Therefore, the human body demand needs to be calculated according to age, height, body weight, labor intensity and the like, the foods to be matched and the usage amount are calculated according to the nutrients contained in different foods and accompanying components thereof, the above calculating processes are complex and not easy to implement. That's because it is necessary to manage both the changing ingredients of foods and the effects of different food ingredients on blood glucose. More importantly, food usually contains both the ingredients the patients needs and the ingredients the patients does not need, so the selected food will affect the nutritional composition and the changes of blood glucose, moreover, the patients are required to change their habits. Therefore, for the patients who are non-medical staff, it is hard to study, operate, control the quality and change the habits; and for the medical staff, in fact it is not easy to explain.

Therefore, a lot of simple methods such as the dietary guide pyramid, the food exchange list and the like are developed, thus the calculations are avoided. However, since the defects of natural foods are not improved, simplify shall be at the expense of the loss of quality.

Therefore, although everyone knows a scientific diet, most methods are not correct. The more the patients are treated, the more the patients are, and the patients cannot be cured, the complications cannot be prevented. All hypoglycemic techniques can lead to the blood glucose being out of control. Because the fact that the disease prevention and etiological factors are ignored, the risk factors of complications are numerous, and only the blood glucose level is reached, and the hypoglycemic agents cannot be effectively used when blood glucose is too low due to the instability of blood glucose in the diet.

Moreover, in fact, as long as the dietary energy management is involved, almost all the results of disease prevention and control are the same. For example, currently in china, there are not only 1.139 billion diabetic patients, 1.9 billion pre-diabetic patients, but also 2 billion patients with hyperlipidemia and 3 billion patients with obesity at the same time, and more patients with diseases caused by diet independently or diet combined with other causes such as hypertension and other series of diseases. Other countries have no exception, and lipid-lowering technologies are associated with coronary heart disease which is one of the highest mortality rates in humans.

As there are no appropriate tools, no one can achieve a good result. Any technique which cannot be achieved or cannot guarantee the quality is an unsuccessful technology, but the patients still suffer from the disease as there is no way to avoid and there is no method can solve the problem of patient's diet.

People may not agree with the above opinion, they think there are already many diabetic foods such as sugar-free foods, blood glucose-lowering foods, foods rich in vitamins and minerals and the like. Yes, but most of these foods cannot help diabetic patients to manage dietary energy. For example, the sugar-free foods are just not added with sucrose, but they still contain starch and other carbohydrate foods and the contained protein is still in a small amount and in poor quality, the high-quality protein still needs to be eaten together with the accompanying saturated fat; the blood glucose-lowering foods are mainly the foods which can lower the blood glucose as the name suggested, however, the aim of the nutrition management of diabetes is to correct the metabolic disorders by limiting when the foods or nutrition are too much or supplementing when the foods or nutrition are too little; although vitamins, minerals and the like are parts of the contents of dietary management for diabetes, they cannot replace the energy management.

Therefore, National Center for Disease Control of China released a multi-sector census report on diabetes on 9 Jan. 2012, and the report clearly pointed out that Chinese generally lack the awareness of prevention and control of diabetes and the related knowledge and skills. Especially as the risk factors such as unreasonable dietary and the like exist, the biological factors such as overweight, obesity, hypertension, impaired glucose tolerance and the like increase rapidly, if such situation cannot be effectively controlled, the number of diabetic patients in China will continue to increase dramatically.

Actually, the reasons behind many diseases are that the current technologies are unable to adapt to food deficiencies, as a result, most people with normal pancreatic function need to lower the blood glucose levels; excessive exercise and the use of hypoglycemic agents aggravate metabolic disorders such as lipometabolism and proteometabolism and the like, and then aggravate the type 2 diabetes and risk factors of complications such as hyperlipidemia, hypertension, hypoimmunity and the decrease of the ability to repair human tissues and the like. Meanwhile, the blood glucose in the diet is not stable, the closer the blood glucose level and the normal level are, the higher the mortality is, that's why it is hard to avoiding death even if the patient is in a hospital and around with a doctor, the only thing is let hyperglycemia complications appear. However, most of these diseases can be cured, and most complications can be prevented.

Although the causes of diabetes are numerous, most diabetes are type 2 diabetes which are caused by increased lipid metabolisms and can be relieved, these patients always have normal pancreatic functions. Therefore, for the type 2 diabetics, pancreas islet cannot play hypoglycemic effect as the increased lipid metabolisms prevent the blood glucose from entering cell metabolism channels. Type 2 diabetics is completely different from type 1 diabetes which are caused by the reduction of insulin as the factor such as infection, immunity, trauma, the physical and chemical injury and the like directly impair the islet function. Nevertheless, most patients do not loss their pancreatic function completely.

Therefore, as long as the diet is scientifically managed, or under the premise of meeting the normal need of protein and carbohydrates, only the saturated fat is reduced, hypoglycemic effect will be naturally played, and most patients will be naturally cured, meanwhile the blood lipid and blood pressure will be naturally regressed, and the complications such as fatty plaques in the cardiovascular and cerebrovascular will be naturally prevented and reversed. Therefore, even if few patients have islet function failure, the hypoglycemic therapeutic agent still needs to be treated, the degree of resulting damage is very limited, and most complications will not occur. This is because the human body originally is a natural biological function system, when the risk factors of etiology and complications relieve, the self-ability of the human body naturally appears. It is completely different from the additional abilities obtained from medicines and the like.

SUMMARY OF THE INVENTION

In order to improve the quality of dietary management for diabetes and keep the blood glucose level stable, the present invention corrects the metabolic disorders from the origin by limiting when the foods or nutrition are too much or supplementing when the foods or nutrition are too little by applying the law which is too much or too little nutrition affect the human health and cause disease. The present invention relieves the cause of type 2 diabetes, reduces the risk factors leading to complications and saves hypoglycemic agents, meanwhile improves the situation that hypoglycemic agents cannot be safely and effectively used due to the affection of the diet, thereby improving the systematical therapy. The present invention provides a specialized flour for diabetic nutrition meals which is mainly for diabetic patients to improve the following problems: in the natural state, high-protein foods are accompanied by high-fat; high-dietary fiber foods such as roughage are accompanied by high-starch and small amounts of poor quality proteins; the compositions of foods change due to the influence of various factors; the calculation is complex for managing the diabetes diet; the food matching process is complicated; different ingredients can interact with each other; and the related factors causing the changes of blood glucose levels are not easy to determine. The present invention improves the blood glucose and blood lipid levels, reduces the complications and saves the hypoglycemic agents. The present invention makes the living habit easy to implement, stabilizes and slows the digestion and absorption, and lowers the postprandial blood glucose when matching with starches, and meanwhile it is conducive to the safe and effective use of the hypoglycemic agents.

The above object of the present invention is achieved by the following technical solutions.

The present invention provides a kind of specialized flour for nutrition meals of diabetes, the flour uses cereal flour such as wheat, oat and rice and glutinous rice and the like as a base material, and is prepared by adding vegetable proteins such as defatted soybean and the like, and dietary fiber such as the separated soybean tissue and the like, and then physical mixing under normal pressure, the protein content of the obtained specialized flour is 20-26 wt % on a dry basis, the dietary fiber content is 4-10 wt %, the carbohydrate content such as starch is 65 wt % or less, and the fat content is 4 wt % or less.

When uses cereal flour such as wheat, and oat and the like as the base material, the flour of the present invention is mainly used for making steamed buns, noodles, baked pancake, bread and other kinds of homemade and convenient foods; and when uses cereal flour such as rice and glutinous rice and the like as the base material, the flour is mainly used for making rice noodles and other kinds of homemade and convenience foods.

Hereinafter the technical solution of the present invention will be described in detail.

In one aspect, the present invention provides a flour specialized for diabetic nutrition meals, the flour adopts cereal flour as the base material and added with defatted soya vegetable protein powder and dietary fiber powder isolated from soybean tissues, wherein the content of protein is 20-26 wt %, the content of dietary fiber is 4-10 wt %, the content of carbohydrate (such as starch) is 65 wt % or less, and the content of fat is 4 wt % or less based on dry basis of the flour.

Preferably, the cereal flour is selected from wheat flour, oat flour, rice flour and glutinous rice flour.

Preferably, the content of protein is 23 wt %, the content of dietary fiber is 8 wt %, the content of carbohydrate is 65 wt % or less, and the content of fat is 4 wt % or less based on dry basis of the flour;

preferably, for patients who use the flour for the first time and are in the use of hypoglycemic drugs, for example, for inhibiting carbohydrate absorption, such as α-glycosidase inhibitors, for promoting the peripheral metabolism of blood glucose, such as biguanides, and for inhibiting gluconeogenesis, such as pancreozymin, the flour adopts cereal flour as the base material and added with defatted soya vegetable protein powder and dietary fiber powder isolated from soybean tissues, wherein the content of protein is 26 wt %, the content of dietary fiber is 8 wt %, the content of carbohydrate is 61 wt %, and the content of fat is 4 wt % or less based on dry basis of the flour, the remaining is other normal food ingredients, such as ash;

more preferably, for patients who use the flour for the first time and are in the use of hypoglycemic drugs, for example, for promoting insulin secretion, such as sulfonylureas and for sensitizing insulin, such as glinides, or are in the use of insulin directly, the flour adopts cereal flour as the base material and added with defatted soya vegetable protein powder and dietary fiber powder isolated from soybean tissues, wherein the content of protein is 24 wt %, the content of dietary fiber is 8 wt %, the content of carbohydrate is 63 wt %, and the content of fat is 4 wt % or less based on dry basis of the flour, the remaining is other normal food ingredients, such as ash;

further preferably, for patients who have already used the flour, the flour adopts cereal flour as the base material and added with defatted soya vegetable protein powder and dietary fiber powder isolated from soybean tissues, wherein the content of protein is 22 wt %, the content of dietary fiber is 6 wt %, the content of carbohydrate is 65 wt %, and the content of fat is 4 wt % or less based on dry basis of the flour, the remaining is other normal food ingredients, such as ash;

most preferably, for patients whose blood glucose level and blood lipid level have returned to normal, whose conditions are not so serious or who have a normal blood lipid level and need to use a small amount of hypoglycemic drugs for maintaining stable blood glucose level, the flour adopts cereal flour as the base material and added with defatted soya vegetable protein powder and dietary fiber powder isolated from soybean tissues, wherein the content of protein is 20 wt %, the content of dietary fiber is 10 wt %, the content of carbohydrate is 65 wt %, and the content of fat is 4 wt % or less based on dry basis of the flour, the remaining is other normal food ingredients, such as ash.

In another aspect, the present invention provides a method for preparing the above flour, comprising mixing the cereal flour, the defatted soya vegetable protein powder and the dietary fiber powder isolated from soybean tissues by physical methods under normal pressure.

In yet another aspect, the present invention provides a food product or semi-finished product, which is prepared from the flour.

In still another aspect, the present invention provides a use of the flour or the food product or semi-finished product in the preparation of a medicament for the prevention and/or treatment of diabetes.

In a further aspect, the invention provides a method for preventing and/or treating diabetes, comprising administering to a diabetic individual the food prepared from the flour.

The principle of the specialized flour is as follows:

The aim of reducing the intake of meat, eggs and milk and the intake frequencies of these substances is to reduce the intake of saturated fats. The resulting reduced protein is replaced by optimized ingredients such as defatted soybean protein according to different nutritional management needs, living habits and matching needs, and the optimized ingredients are added into the staple foods, meanwhile high-quality dietary fibers are also added thereinto on demand. The purpose of doing so is to correct diabetes metabolic disorders, stabilize and reduce the postprandial blood glucose, meet the dietary nutritional management needs, and solve the difficulties for patients to learn, perform, control the quality, and change their living habits and compliance, which caused by the following deficiencies: the meat, eggs and milk are accompanied by high-fat, the roughage is accompanied by high-starch (carbohydrates), the protein is small in amount and poor in quality.

Because in diabetes, (1) enough high-quality protein and small-molecule high-quality dietary fibers match with each other to effectively wrap up the starch, so that the starch can be digested and absorbed with comprehensive nutrition and be naturally and slowly released into blood, so the patients can metabolize the blood glucose through their residual islet function and exercise without additional hypoglycemic agents or insulin, thereby lowering the postprandial blood glucose and reducing the need for hypoglycemic agents; (2) the present invention can stabilize the blood glucose levels, and can naturally improve the situation that hypoglycemic agents cannot be safely and effectively use due to the limitation of hypoglycemia; (3) The flour of the present invention can realize the nutritional management goal characterized by that the saturated fat is significantly lower, the protein is slightly higher and the carbohydrate (saccharide) is slightly lower compared with normal human beings as described in the book Medical Nutrition Therapy Guidelines for People with Diabetes Mellitus; correct naturally the irrational dietary habits before suffering from diabetes and the high blood glucose level after suffering from diabetes; improve the symptoms such as the decrease and delay of the output of the energy from carbohydrates, glucosuria, hyperfunction of fat anabolism and catabolism and increased protein consumption in the process of replacing carbohydrates with protein and fat to sustain life, and naturally increase the working efficiency and sensitivity of insulin secreted by the pancreatic island. That's because excess fat metabolism not only can increase blood lipids and damage blood vessels, but also can hinder blood glucose into cellular metabolic process, which causes that the working efficiency of insulin which can only transfer blood glucose on the cell surface reduces, thus, the islet will not play a normal hypoglycemic effect even if it has a normal function. Moreover, excess fat metabolism also causes damage inflammatory cells surface and increased insulin insensitivity due to the accumulation of free fats. Therefore, diabetes has a high incidence in overweight people, people who do not eat breakfast, and old people who have decreased basal metabolism and reduced motion. Therefore, the reduction of total fat metabolism will naturally improve the blood glucose and blood lipids, while naturally reduce the cardiovascular and cerebrovascular complications at the same time; (4) the present invention reduces the effect on protein and fat metabolism from the blood glucose metabolism and meet the basic needs for carbohydrate foods. That's because gluconeogenesis exists in human body, other substances will automatically supplement if the carbohydrates from foods is not enough. Therefore, inadequate intake of carbohydrates not only cannot reduce the burden of islet, but also needs to call more protein and glycerol in fat to convert due to very little liver glycogen reserves, further needs more protein and fat instead of carbohydrate to directly burn to sustain life. The process aggravates the burden of pancreatic islet thus reducing the working efficiency of insulin, and also aggravates the fat and protein metabolic disorder and causes the complication. As the whole process simulates the basic pathology of the glucose metabolism in diabetes, the diabetic diet should prevent too much or too little carbohydrate.

The present invention can naturally improve blood lipids: (1) the saturated fat can be reduced by reducing the intake of meat, eggs and milk, the resulting reduced protein is provided by the reinforced optimized staple food and vegetable protein, which directly reduces the fat source and its metabolic process, and reserves a space for improving life and keeping the original eating habits; (2) the needs for carbohydrate foods such as starch are guaranteed. This not only avoids excessive energy cannot be consumed and thus the fat is synthesized, but also avoids the fat and protein are decomposed to provide energy due to insufficient starch thus the fat through the blood is reduced; (3) the normal needs for protein are guaranteed. The carrying capacity on fat is naturally improved. The intake on more staple foods, which can be converted to fat due to hungry caused by lacking of protein, and more cooking oil, which can directly raise the blood lipid is avoided, when the free fat is naturally reduced, the blood lipids is elevated, the blood viscosity is increased and the complications is reduced; (4) high-quality dietary fibers can not only absorb fat, naturally improve blood lipids, but also can improve the intestinal probiotics and reduce the lipocatabolic injury caused by bacteria such as enterobacter cloacae and endotoxin.

The present can reduce naturally weight, and protect the effect of losing weight as one of the dietary management goals is to reduce the total fat and its metabolic process.

Compared with the prior arts, the specialized flour of the present invention has the following beneficial technical effects:

Compared with common foods, the specialized flour of the present invention is more convenient, the effect is more significant and the postprandial blood glucose is lower and more stable when achieving the same diabetic dietary management goal. It is convenient for doctors to explain, for patients to learn and use, and it is no longer change eating habits. For example, only the specialized flour of the present invention can be used to instead of the staple food in the same amount to make foods, meat, eggs and milk are reduced and vegetables are basically unchanged at the same time, after doing this, a normal level can be obtained. It is also convenient to adjust, calculate and match with other foods later. Therefore, the restrictions, interference and damage caused by incontrollable diet were reduced, metabolic disorders are easily corrected, and the risk factors of complications such as hyperlipidemia, hypertension, immunity and tissue repair capacity decreased are naturally prevented and reversed thus naturally reducing the complications. Meanwhile, the situation that hypoglycemic agents cannot be safely and effectively used is improved.

The specialized flour of the present invention adds the dietary fiber powder isolated from soybean tissues and increases the amount of dietary fibers. This is because the inventors found that the dietary fibers can combine with vegetable proteins such as defatted soybean and the like to co-wrap the edible starch to stabilize the rate of its digestion and absorption thereby reducing steadily the postprandial blood glucose levels. In addition to saving the hypoglycemic agents, the present invention also can effectively improve the situation that the hypoglycemic agents can not be safely and effectively used, and further improve current blood glucose management problem, which is letting the blood glucose out of control. Meanwhile, the present invention can improve the blood glucose level by the following ways: inhibiting gluconeogenesis by promoting pancreozymin; driving the insulin by promoting protease; improving the beneficial bacteria in the intestinal and reduce endotoxin such as lipopolysaccharide and the like from mixed bacteria, and increasing the working efficiency of insulin.

The present invention uses dietary fiber powder isolated from soybean tissues, that's because that the inventor of the present invention found that different sources of dietary fibers from had different effects on the postprandial blood glucose. The improvement of dietary fibers on the blood glucose levels attribute that the molecules at both ends of the fibers can combine with water and form gel, which then affects the gastrointestinal motility and the digestion and absorption of food nutrients rather than the function when entering the human body. Therefore, the dietary fiber is neither the more the better nor the same with each other the better, the instability of the blood glucose levels cause that the hypoglycemic agents can not be used safely and effectively. In addition, cereal dietary fibers not only have large molecules, less water absorption and gel formation and poor effect on the improvement of the blood glucose levels but also accompany with high content of starch and small amount of poor quality protein. The content of the dietary fibers in other sources such as general stalk and foliage vegetables is only 1%-2%. The amount of dietary fibers is more than 30 g per day according to the recommendations of evidence-based medicine, which will require more than 2 kg of vegetables. Different types of dietary fibers result in different changes of postprandial blood glucose, and also can lead to the imbalance of other nutrients such as vitamins, minerals and others, and the bad taste and performance of the produced foods. The dietary fiber powder isolated from soybean tissues belongs to semi-soluble dietary fibers, does not have the drawback that smaller molecular dietary fibers such as sodium alginate and the like affect the blood pressure due to carrying metal ions, and has a better and more stable effect on reducing the blood glucose compared with cereal dietary fibers. Meanwhile, the foods prepared by the dietary fiber powder isolated from soybean tissues taste fine and have better performance as the influence of the dietary fiber powder isolated from soybean tissues on the food performance is relatively small.

Compared with ordinary foods, the foods prepared by the flour of the present invention solve the problems which cannot be solved by ordinary foods. it is difficult for ordinary foods to achieve the dietary management goals in high quality and stabilize the postprandial blood glucose at the same time, therefore, any conventional hypoglycemic technology will cause the blood glucose out of control, thus the diabetes cannot be cured and the complications cannot be prevented. There is currently no large-scale clinical study on the technical solutions which can achieve the nutrition management goals similar to that of the present invention in diabetes, the goals are only mentioned in the book Medical Nutrition Therapy guidelines for people with diabetes mellitus, but in which no more detailed information is available. Some related studies are as follows: China Da Qing Diabetes Prevention Study ended in 1992, American Diabetes Prevention Program (DPP) ended 1999, Finnish Diabetes Prevention Study (DPS) ended in 2001 and European Stop-DIDDM study ended in 2002. However, since these studies do not establish food management tools, the risk of diabetes is only reduced by 58%-71%. Therefore, it is difficult to avoid the deformation of the nutritional management during the implementation process.

Nevertheless, the China Da Qing Diabetes Prevention Outcome Study ended in 2006 found that the morbidity of the patients, who were intervened by the substances in which the fat accounts for 25%-30% of total energy for six years, was only 43% after 20 years, which was far less than that of the patients who had never experienced such intervention (the morbidity was 92%). Meanwhile, the mortality of the intervened patients was dropped significantly due to suffering from the cardiovascular and cerebrovascular diseases and all factors. That is to say, this study also shows that the diet has huge prevention values for diabetes and complications thereof.

Compared with the nutrition treatment using the supplements such as vitamin and mineral, the present invention belongs to different types of nutrition management systems, and uses the law which is too much or too little nutrition affect the human health and cause disease. The use of the supplements such as vitamin and mineral can not be replaced. Although the present invention does not described that the specialized flour of the present invention contain the supplements, in fact, the supplements have been intaken according to the normal need when matching with other foods such as vegetables. As diabetes is a kind of energy metabolism disorders, and the complications are mainly caused by the energy metabolism disorders such as hyperglycemia, hyperfunction of fat anabolism and catabolism and increased protein consumption. Although the supplements such as vitamin and mineral are very important, they are not major.

Compared with sugar-free foods, the present invention also has many advantages. In fact, sugar-free foods are a pseudo-concept. A food is called a sugar-free food in that the food is not added with sucrose, however, there are various sugars in foods. For example, the sugars are not only widespread in the foods such as fruit, honey, beverages and others, but only widespread in the foods which almost cannot be eaten by people such as vegetables, cereals, beans and others, and the amount is higher. Moreover, although carbohydrates may be in the form of monosaccharide such as glucose, fructose, galactose and others; disaccharide such as sucrose (two fructose), lactose (galactose plus glucose), maltose (two glucose) and others; polysaccharide such as starch, dextrin and others, however, they can be absorbed and utilized only when being digested or decomposed into monosaccharide. Therefore, such substances are collectively referred to as carbohydrate or sugar.

More importantly, carbohydrates are the largest and indispensable green energy source, which not only participate in forming many life substances, help the fat to completely burn, protect the liver from toxic damage, but also ensure continuous energy supply of important organs of human bodies. Low concentration of carbohydrates will endanger the life. Therefore, the intake of too little carbohydrates not only fails to reduce the burden of islet but also accelerates the decreases of work efficiency in insulin and the complications. That's because the blood glucose can be timely supplemented through gluconeogenesis. Therefore, even if no carbohydrate is intaken, the blood glucose still rises, the protein will be consumed excessively and the fat anabolism and catabolism will be increased. Thus, the type II diabetes is aggravated and the complications such as cardiovascular diseases, the reduced repair capacity of large blood vessels, immunity and tissues are accelerated. Because the carbohydrates cannot provide energy in time, the life activities such as breathing, heartbeat and others are still going on, the body will automatically mobilize protein and fat to make up, otherwise life will not be able to continue normally, this process simulates diabetic glucose metabolism disorders. Therefore, sugar-free foods are not only useless for the nutrition management of diabetes, but also will lead to a confusion concept.

Compared with various functional foods such as hypoglycemic foods and hypolipidemic foods and the like, the present invention also has many advantages. There is no doubt that foods not only contain nutrients but also contain a lot of components for adjusting the body's function which is similar to medicines, such as saponin, flavonoe, isoflavone and flavonoid, heteropolysaccharide, polysaccharide, polyunsaturated fatty acid, collagen and its degradation peptide, nucleic acid, microelement selenium, trivalent chromium and the like, they either help the body to remove peroxides or improve the body's metabolic capability on fat and glucose. There are some currently unknown food ingredients, which can also be used for treating diabetes, for examples the medicinal and edible foods such as radix ophiopogonis, lily, Chinese yam, medlar and others.

Such foods however differ from the natural law used in the present invention. The law used in the present invention is that energy affects the nutrition, which is too much or too little nutrition affect the human health and cause disease. The law works whether or not to eat. The present invention can limit when the foods or nutrition are too much or supplement when the foods or nutrition are too little according to the nutritional status of individuals and the need for consumption. That is to say, the excess nutrients are reduced while the increased consumption needs are met, thus, the blood glucose and blood lipid can be naturally improved by the body's own ability. That's because the islet functions and insulin secretion capacity of most patients with type 2 diabetes are always normal, although the islet functions of patients with other types of diabetes have injury to some extent, are not completely damaged. The hypoglycemic or hypolipidemic foods are similar to hypoglycemic agents, they only can give the body additional capacity, cannot reduce the disease by intaking fat and complications thereof. Therefore, although they are also foods, but they affect the law and their working rules are completely different from that of the flour of the present invention.

DETAILED DESCRIPTION OF PREFERRED EMBODIMENTS

The present invention will be further described in detail in combination with the embodiments hereinafter. It should be noted that the embodiments provided are only used to illustrate the present invention, rather than limiting the scope of the present invention.

Unless otherwise indicated, the experimental methods in the following embodiments are all conventional methods. Unless otherwise indicated, the raw materials and other materials used in the following embodiments are all commercially available.

Unless otherwise indicated, the percentages used in the following embodiments are mass percentages, i.e., mass/mass.

1. Production Example

The production index of the specialized flour of the present invention is set as follows: the content of protein is 23 wt % or more ($\geq 23\%$), the content of dietary fiber is 8 wt % or more ($\geq 8\%$), the content of carbohydrate is 65 wt % or less ($\leq 65\%$), and the content of fat is 4 wt % or less ($\leq 4\%$).

The raw materials which meet the national standard are purchased, the indexes of these raw materials are detected and the results are as follows: (1) superfine refined wheat flour: containing 10.3% of protein, 74.6% of starch, 1.1% of fat, 0.6% of dietary fiber and 12.7% of water; (2) rice flour: containing 7.8% of protein, 77.8% of starch, 0.8% of fat, 0.6% of dietary fiber and 12.9% of water; (3) defatted soya vegetable protein powder (defatted soya protein isolate powder): containing 92.1% of protein, 0.8% of fat, 0.8% of dietary fiber and 5.9% of water; (4) dietary fiber powder isolated from soybean tissues: containing 20% of protein, 71% of dietary fiber, 1.6% of fat, 1.2% of starch and 5.9% of water.

Production method 1: 100 kg specialized flour was prepared from the superfine refined wheat flour as a base material (was made into foods such as steamed buns). The usage amount of the superfine refined wheat flour was set to x, the usage amount of the defatted soya protein isolate powder was set to y, and the usage amount of the dietary fiber powder isolated from soybean tissues was set to z. The following equations should be satisfied:

$$x+y+z=100 \text{ (weight)}; 10.3\% \ x+92.1\% \ y+20\% \ z=23 \text{ (protein)}; 0.6\% \ x+0.8\% \ y+71\% \ z=8 \text{ (dietary fiber)}.$$

After calculation, the usage amounts of raw materials are obtained as follows:

the superfine refined wheat flour: 75.25 kg;
the defatted soya protein isolate powder: 14.28 kg;
the dietary fiber powder isolated from soybean tissues: 10.47 kg.

Production method 2: 100 kg specialized flour was prepared from the rice flour as a base material (was made into mechanism rice). The usage amount of the rice flour was set to $x1$, the usage amount of the defatted soya protein isolate powder was set to $y1$, and the usage amount of the dietary fiber powder isolated from soybean tissues was set to $z1$. The following equations should be satisfied:

$$x1+y1+z1=100; 7.8\% \ x1+92.1\%+20\% \ z=23; 0.6\% \ x1 \ 0.8\% \ y+71\% \ z1=8.$$

After calculation, the usage amounts of raw materials are obtained as follows:

the rice flour: 73.02 kg;
the defatted soya protein isolate powder: 16.52 kg;
the dietary fiber powder isolated from soybean tissues: 10.46 kg.

The production flow is as follows: checking the information such as the production requirements, the origin of the raw materials, the process formula, the packaging materials, the production date and the shift number and so on, weighing the raw materials—importing into a dry powder mixing machine through a feeding hopper—mixing physically under normal temperature and pressure for 20 minutes—pouring into a discharging hopper—conveying—packaging and weighing by a packaging machine—putting in storage.

The specialized flour having different nutrient compositions of the present invention can be obtained by using the same method. For example, the following flour can be obtained: (1) 26 wt % of protein on a dry basis, 8 wt % of dietary fiber, 61 wt % of carbohydrate, and 4 wt % or less of fat; (2) 24 wt % of protein on a dry basis, 8 wt % of dietary fiber, 63 wt % of carbohydrate and 4 wt % or less of fat; (3) 22 wt % of protein on a dry basis, 6 wt % of dietary fiber, 65 wt % of carbohydrate and 4 wt % or less of fat; (4) 20 wt % of protein on a dry basis, 10 wt % of dietary fiber, 65 wt % of carbohydrate and 4 wt % or less of fat. These formulations are to meet different demands, such as different nutrition status, different food match, and different diabetic patients to make the nutrition management or steadily lower the postprandial blood glucose. That's because that the usage amount of the specialized flour of the present invention will vary depending on the content of the nutrients and dietary fiber in other foods to be matched with under the premise of the same management objective for nutrients such as protein, fat and carbohydrate, and the same amount of dietary fiber.

2. Application Example

Simple method: The daily intake amounts of meat, egg and milk should be reduced. For example, a patient can intake daily one egg, one bag of milk (225 ml) or 25 g lean meat or fish, 600-750 g vegetables, 15-20 g vegetable oil and 30 g coarse cereals porridge such as oat porridge and the like. Meanwhile, the staple food is made from the specialized flour of the present invention instead of the plain flour used originally, The intake amount of the specialized flour is about 300 g for a patient with 1.5 meters tall, the intake amount of the specialized flour is about 350 g for a patient with 1.65 meters tall, the intake amount of the specialized flour is about 400 g for a patient with 1.75 meters tall, and the intake amount of the specialized flour is about 450 g for a patient with 1.85 meters tall. The intake amount of the specialized flour increased with the amount of exercise. If the patient wants to intake other food, the intake amount should be calculated according to the factors such as age, height, body weight, and labor intensity.

Calculation method 1: as for an overweight patient, if her/his exercise amount is not changed, the total energy should be reduced by 300 kilocalories, wherein, the energy transferred from the fat from meat, egg and milk should account for 70% or more, the staple food is made from the specialized flour of the present invention instead of the plain flour used originally, and supplemented by coarse cereals such as the oat and vegetables until the required amount is reached;

Calculation method 2: the body's demand for food can be calculated according to the factors such as age, height, body weight, and labor intensity and the like. Wherein, the total energy is controlled in accordance with the criterion of an ideal body weight, the protein accounts for 15%-20% of the total energy or the intake amount is 1.2 g per kilogram of body weight daily; the fat accounts for 25% or less, in which the saturated fat accounts for 7% or less; the total carbohydrate including starch account for 55%-60%, the amounts range plus or minus 10%. The amounts of these nutrient substances can be adjusted according to the indexes such as body weight, blood lipid and blood glucose.

Optimization and group method of nutrition compositions: if a patient has no experience in nutrition arrange and medicine adjustment when facing with the changes in diet, other food should be reduced, thus a relatively more complete and effective diet nutrition and blood glucose change can be controlled, thereby facilitating the blood glucose monitoring and medicine and adjustment, then selecting other foods according to the monitoring results. Nutrition management is not a simple management for foods but for nutritional compositions of all foods. Nutritional status, exercise and dosage of different patients have different effects on nutrient consumption and thus different nutritional management objectives are required. For example, the simultaneous consumption of three types of energy in human body increase with the amounts of exercise; the use of hypoglycemic drugs, for example, for inhibiting carbohydrate absorption, such as α-glycosidase inhibitors, for promoting the peripheral metabolism of blood glucose, such as biguanides, and for inhibiting gluconeogenesis, such as pancreozymin reduces the capacity of carbohydrates and increases the consumption of protein. However, the use of hypoglycemic drugs, for example, for promoting insulin secretion, such as sulfonylureas and for sensitizing insulin, such as glinides, or the use of insulin directly reduces the consumption of protein. Meanwhile, since most patients are overweight, if the total energy is provided according to the desired body weight, the protein should be provided based on kilogram of body weight. Therefore, the tools which can contain different contents of protein and dietary fiber should be set or different pre-formulated foods should be prepared according to different needs for nutrition management and different foods, otherwise, it is easy for the diet to become into a interference factor.

For example, (1) for patients who use the flour for the first time and are in the use of hypoglycemic drugs, for example, for inhibiting carbohydrate absorption, such as α-glycosidase inhibitors, for promoting the peripheral metabolism of blood glucose, such as biguanides, and for inhibiting gluconeogenesis, such as pancreozymin, they can select the food made from the specialized flour of the present invention comprising 26 wt % of protein on a dry basis, 8 wt % of dietary fiber, 61 wt % of carbohydrate and 4 wt % or less of fat. The total energy for maintaining an ideal body weight is calculated according to the factors such as age, height, body weight, exercise and labor intensity, wherein, the average intake amount of protein is 1.4 g per kilogram of body weight daily; the fat accounts for 20% or less, wherein the saturated fat accounts for 7% or less; the total carbohydrates including starch account for 55%, the amounts range plus or minus 10%. Only 500-700 g raw or boiled cool green leafy vegetables are intaked. Vegetable oil is controlled within 10 g per day.

For patients who use the flour for the first time and are in the use of hypoglycemic drugs, for example, for promoting insulin secretion, such as sulfonylureas and for sensitizing insulin, such as glinides, or are in the use of insulin directly, the food made from the specialized flour of the present invention comprising 24 wt % of protein on a dry basis, 8 wt % of dietary fiber, 63 wt % of carbohydrate and 4 wt % or less of fat can be selected. The total energy for maintaining an ideal body weight is calculated according to the factors such as age, height, body weight, exercise and labor intensity, wherein, the average intake amount of protein is 1.2 g per kilogram of body weight daily; the fat accounts for 20% or less, wherein the saturated fat accounts for 7% or less; the total carbohydrates including starch account for 55%, the amounts range plus or minus 10%. Only 500-700 g raw or boiled cool green leafy vegetables are intaked. Vegetable oil is controlled within 10 g per day. The blood glucose at the following 7 time points should be monitored: three times a day before meals, 2 hours after meals and midnight, the medicine can be adjusted according to the change of blood glucose. For example, if the blood glucose level goes beyond the range of 6-7 mmol/L for before meals or 8-10 mmol/L for 2 hours after meals, the medicines should be correspondingly adjusted. If the blood glucose level is stable, the frequency of monitoring can be reduced.

(2) For patients who have already used the flour, have experience in nutrition arrange and medicine adjustment when facing with the changes in diet or have less severe metabolic disorder, the food made from the specialized flour of the present invention comprising 22 wt % of protein on a dry basis, 6 wt % of dietary fiber, 65 wt % of carbohydrate and 4 wt % or less of fat can be selected. The total energy for maintaining an ideal body weight is calculated according to the factors such as age, height, body weight, exercise and labor intensity, wherein, the average intake amount of protein is 1.2 g per kilogram of body weight daily; the fat accounts for 20% or less, wherein the saturated fat accounts for 7% or less; the total carbohydrates including starch account for 55-60%, the amounts range plus or minus 10%. According to personal habits, one egg or one bag of milk (255 ml), or 25 g lean meat or fish, or 30-50 g coarse cereals such as oat can also be used daily. The nutrition of these foods is also added for calculation.

(3) For patients whose blood glucose level and blood lipid level have returned to normal, whose conditions are not so serious or who have a normal blood lipid level and need to use a small amount of hypoglycemic drugs for maintaining stable blood glucose level, the food made from the specialized flour of the present invention comprising 20 wt % of protein on a dry basis, 10 wt % of dietary fiber, 65 wt % of carbohydrate and 4 wt % or less of fat can be selected. The total energy for maintaining an ideal body weight is calculated according to the factors such as age, height, body weight, exercise and labor intensity, as the protein consumption reduces, the nutrition composition should be adjusted into: the protein accounts for 15 wt %, the fat accounts for 20-30%, wherein the saturated fat accounts for 7% or less; the total carbohydrates including starch account for 55-60%, such composition is suitable for normal human beings and allows to match with other foods. If it appears imbalance, the above scheme (1) or (2) may be repeated.

3. Experiment Example (1) 47 type II diabetic patients without nephropathy were treated with the specialized flour comprising ≥23 wt % of protein on a dry basis, ≥8 wt % of dietary fiber, ≤65 wt % of carbohydrate, ≤4 wt % of fat for 4 weeks. The type of the hypoglycemic drugs used by the patients was not changed during observation, only the dosage of the hypoglycemic drugs was adjusted according to the change of blood glucose levels. Results: the postprandial blood glucose levels for all patients were significantly reduced, or the dosage of the hypoglycemic drugs were reduced as the blood glucose levels measured 2 hours after meals were lower than 6 mmol/L (p<0.01). The dosage of the hypoglycemic drugs for total patients was decreased by 46.1%±9.6% (p<0.01). Wherein, the dosage of the hypoglycemic drugs for 17 patients who use insulin and c-peptide and whose blood glucose levels are increased more than 2 times at 2 hours after meals was decreased by 57.9%+8.8% (p<0.01). The dosage of the hypoglycemic drugs for 14 patients who use insulin and c-peptide and whose blood glucose levels are increased more than 3 times at 2 hours after meals was decreased by 69.6%+13.1% (p<0.01). The dosage of the hypoglycemic drugs for 31 patients with high total cholesterol or triglycerides was significantly decreased (p<0.05). In the self-control study, compared with 33 patients who finish the same nutritional management goal by using conventional foods, the blood glucose fluctuation was reduced by 43.1%, the dosage of the hypoglycemic agents was reduced by 25.6% (p<0.01), the average preprandial blood glucose was reduced by 2.3 mmol/L (p<0.01), the average 2-hour postprandial blood glucose was reduced by 5.2 mmol/L (p<0.01). Conclusion: the specialized flour of the present invention can improve significantly the blood glucose levels, and can improve the blood lipid levels at the same time.

(2) 293 type II diabetic patients without nephropathy were treated with the following specialized flours based on if the patients have experience in nutrition arrange and medicine adjustment, the types of hypoglycemic drugs and the changes in blood glucose and blood lipid: (1) 26 wt % of protein on a dry basis, 8 wt % of dietary fiber, 61 wt % of carbohydrate and 4 wt % of fat; (2) 24 wt % of protein on a dry basis, 8 wt % of dietary fiber, 63 wt % of carbohydrate and 4 wt % of fat; (3) 22 wt % of protein on a dry basis, 6 wt % of dietary fiber, 65 wt % of carbohydrate and 4 wt % of fat; (4) 20 wt % of protein in dry basis, 10 wt % of dietary fiber, 65 wt % of carbohydrate and 4 wt % of fat. The above flours were prepared according to the method of the production example. The type of the hypoglycemic drugs used by the patients was not changed during observation, only the dosage of the hypoglycemic drugs was adjusted according to the change of blood glucose levels.

Result 1: the postprandial blood glucose levels for all patients were significantly reduced, or the dosage of the hypoglycemic drugs were reduced or the hypoglycemic drugs were ceased as the preprandial blood glucose levels were lower than 6 mmol/L and the blood glucose levels measured 2 hours after meals were lower than 8 mmol/L (p<0.01). In 126 newly diagnosed diabetic patients, who did not take any hypoglycemic agents, the blood glucose levels for 102 patients returned to normal (i.e., the preprandial. blood glucose levels are lower than 6 mmol/L and the blood glucose levels measured 2 hours after meals are lower than 7.8 mmol/L). The proportion was 80.95%. The remaining 24 patients, whose blood glucose levels were still abnormal, were administered with hypoglycemic agents according to the patient's condition. These remaining patients together with other 167 patients with type II diabetes who have used hypoglycemic agents, totally 191 patients, were included into the follow-up observation. Among them, 22 patients exited the project for various reasons, and 169 patients actually finished the project. Among them, 86 patients stopped using hypoglycemic agents as their preprandial blood glucose levels maintained below 7 mmol/L and their blood glucose levels measured 2 hours after meals maintained 8-10 mmol/L, which accounted for 50.89%. For the remaining 83 patients, the dosage of hypoglycemic agents was reduced by 55.3%±8.8% (p<0.01). Conclusion: the specialized flour of the present invention can improve significantly the blood glucose levels.

Result 2: in 293 type II diabetic patients, 79 patients in 96 patients accompanying with high levels of triglyceride recovered to a normal level, which accounted for 82,29%, and the levels of triglyceride of the remaining patients were significantly decreased (p<0.01). 36 patients in 82 patients accompanying with high levels of total cholesterol recovered to a normal level, which accounted for 43.90%, and the levels of total cholesterol of the remaining patients were significantly decreased (p<0.05). Conclusion: the specialized flour of the present invention can improve significantly the blood lipid levels.

4. Experiment for Selecting Dietary Fibers

The example was designed to investigate the influence of different types of dietary fibers on postprandial blood glucose. Because the fact that the changes in postprandial blood glucose of diabetes induced by dietary fibers such as wheat bran dietary fibers, soybean skin dietary fibers, common vegetables and other dietary fibers are close, the soluble dietary fibers such as sodium alginate carry the electrolytes which affects blood pressure or when adding them into foods, the taste and flavor of the foods become bad, the wheat bran dietary fiber and the dietary fiber isolated from soybean tissues were selected and compared in this experiment.

The preparation method of the food comprises the following steps: 50 grains of wheat starch was taken and was added with the wheat bran dietary fiber (treated with amylase and protease, dried, grinded and screened through a 50 mesh sieve) or the dietary fiber isolated from soybean tissues (treated with amylase and protease, dried, grinded and screened through a 50 mesh sieve), the amount of the wheat bran dietary fiber or the dietary fiber isolated from soybean tissues was 5% or 10% based on the total weight.

Methods: steamed buns as experiment foods (4 kinds of experiment foods, which were made from the flours prepared above) were prepared, 30 patients with type II diabetes were respectively self-controlled. Before experiment, 50 g glucose was intaken, the preprandial blood glucose levels and the postprandial blood glucose levels measured 30-minute, 60-minute, 90-minute, 120-minute, 150-minute and 180-minute after meals were monitored and plotted to form a curve. In the next morning, the experiment foods were administered to the patients. In the experiment, each half of the patients was taken and drawn, and then respectively cross-grouped, and then exchanged every other day. The preprandial blood glucose levels and the postprandial blood glucose levels measured 30-minute, 60-minute, 90-minute, 120-minute, 150-minute and 180-minute after meals were monitored and plotted to form a curve.

Results: the areas under the curve in the groups fed the 5% and 10% wheat bran dietary fiber accounted for 93% and 75% of the area under the curve in the glucose group. The areas under the curve in the groups fed the 5% and 10% dietary fiber isolated from soybean tissues accounted for 67% and 55% of the area under the curve in the glucose group. That is to say, the addition of the dietary fiber isolated from soybean tissues into the wheat starch has a significant effect on ˉimproving the postprandial blood glucose of the type II diabetic patients, the action of the dietary fiber isolated from soybean tissues is obviously superior to that of the wheat bran dietary fibers (p<0.01); and the effect of improving the postprandial blood glucose by using the 5% dietary fiber isolated from soybean tissues is better than that by using the 10% wheat bran dietary fibers. Meanwhile, the steamed buns made from the flour added with the dietary fiber isolated from soybean tissues taste fine, while the steamed buns made from the flour added with the wheat bran dietary fibers are rough, taste bad and have poor color. That is to say, the dietary fiber isolated from soybean tissues has a better adaptability.

Remarks: according to the recommended amount of 30-40 g of dietary fiber daily in combination with the better postprandial glucose reduction effect of the dietary fiber isolated from soybean tissues, meanwhile, taking into account different nutrition management needs or the usage amount of the specialized flour of the present invention when being used with other foods to achieve the same nutrition objective, in the specialized flour of the present invention, the dietary fiber isolated from soybean tissues should account for 4-10 wt % of the flour, in order to maintain relative low and stable postprandial blood glucose levels.

5. Comparative Experimental Example—Improve the Effect of the Postprandial Blood Glucose Levels The specialized flour of the present invention: the flour used wheat flour as a base material, and added with defatted soya vegetable protein powder and dietary fiber powder isolated from soybean tissues, wherein the protein content is 23 wt % on a dry basis, the carbohydrate content is 60 wt %, and the fat content is 4 wt %. The dietary fiber powder isolated from soybean tissues was used, and the content of the dietary fibers is 8 wt % based on dry basis of the flour. The flour was prepared according to the production method 1 of the production example.

Comparative Flour 1: the flour uses wheat flour as a base material, and added with defatted soya vegetable protein powder and dietary fiber powder isolated from soybean tissues, wherein the protein content is 23 wt % on a dry basis, the carbohydrate content is 65 wt %, and the fat content is 4 wt % or less. The dietary fiber powder isolated from soybean tissues was used, and the content of the dietary fibers is 3 wt %. The production method of this flour is the same as that of the specialized flour of the present invention as described above.

Comparative Flour 2: the flour used wheat flour as a base material, and added with defatted soya vegetable protein powder and dietary fiber powder isolated from soybean tissues, wherein the protein content is 23 wt % on a dry basis, the carbohydrate content is 59 wt %, and the fat content is 4 wt %. The dietary fiber powder isolated from soybean tissues was used, and the content of the dietary fibers is 11 wt %. The production method of this flour is the same as that of the specialized flour of the present invention as described above.

Method: 50 g of the specialized flour of the present invention, flour 1 for comparison or flour 2 for comparison was respectively taken and made into steamed buns. 30 patients with type II diabetes were self-controlled. The postprandial blood glucose test was carried out in the next morning, in the experiment, one-third of the patients were taken and respectively cross-grouped, the postprandial blood glucose levels measured 30-minute, 60-minute, 90-minute, 120-minute, 150-minute and 180-minute after meals were respectively monitored and plotted to form a curve.

Results: there were significant differences among the three groups (p<0.05). Wherein, compared with the Comparative Flour 1, the area of the specialized flour of the present invention under the curve reduced by 31.61%, which shows that the postprandial blood glucose levels were significantly improved. However, compared with the Comparative Flour 2, the area of the specialized flour of the present invention under the curve increased by 21.91%.

Remarks: Although the experiment shows that the specialized flour of the present invention has a better effect on reducing the postprandial blood glucose than the Comparative Flour 1 but has a worse effect than the Comparative Flour 2, the experiment actually shows that the postprandial blood glucose levels decrease with the increase of dietary fibers when the contents of protein, fat and carbohydrate keep unchanged. That is to say, if the intake for dietary fibers cannot be effectively managed, the postprandial blood glucose will be unstable, and thus the hypoglycemic agents will not be safely and effectively used. And because of this, any hypoglycemic technology can cause the blood glucose loses control. Because the closer the blood glucose level and the normal level are, the higher the mortality is, that's why it is hard to avoiding death even if the patient is in a hospital and around with a doctor. Meanwhile, it is known that the effect of dietary fibers on reducing postprandial blood glucose attributed that the molecules at both ends of the fibers can absorb water, thereby forming gel. The carbohydrate such as starches for physically wrapping the dietary fibers can delay or reduce the digestion and absorption of the dietary fibers, However, this will affect the nutrition management for proteins, fats, vitamins, minerals and the like at the same time, and these substances are not the more the better. Therefore, in the specialized flour of the present invention, the dietary fiber powder isolated from soybean tissues accounts for 4-10 wt % of the flour. This can maintain relative low and stable postprandial blood glucose levels (wherein, the stable of the blood glucose levels are primary), thereby ensuring that the hypoglycemic agents are safely and effectively used.

6. Comparative Experiment Example—The Saving Effect of Hypoglycemic Agents

The specialized flour of the present invention: the flour uses wheat flour as a base material and added with defatted soya vegetable protein powder and dietary fiber powder isolated from soybean tissues, wherein the protein content is 23 wt % on a dry basis, the carbohydrate content is 60 wt %, and the fat content is 4 wt % based on dry basis of the flour. The dietary fiber powder isolated from soybean tissues was used, and its content is 8 wt %. The flour is prepared by the production method 1 of the production example.

The specialized flour of the present invention is optimized and grouped by nutritional compositions as follows: (1) for patients who use the flour for the first time and are in the use of hypoglycemic drugs, for example, for inhibiting carbohydrate absorption, such as α-glycosidase inhibitors, for promoting the peripheral metabolism of blood glucose, such as biguanides, and for inhibiting gluconeogenesis, such as pancreozymin, the flour adopts wheat flour as the base material and added with defatted soya vegetable protein powder and dietary fiber powder isolated from soybean tissues, wherein the content of protein is 26 wt %, the content of dietary fiber is 8 wt %, the content of carbohydrate is 61 wt %, and the content of fat is 4 wt % or less based on dry basis of the flour; (2) for patients who use the flour for the first time and are in the use of hypoglycemic drugs, for example, for promoting insulin secretion, such as sulfonylureas and for sensitizing insulin, such as glinides, or are in the use of insulin directly, the flour adopts wheat flour as the base material and added with defatted soya vegetable protein powder and dietary fiber powder isolated from soybean tissues, wherein the content of protein is 24 wt %, the content of dietary fiber is 8 wt %, the content of carbohydrate is 63 wt %, and the content of fat is 4 wt % or less based on dry basis of the flour; (3) for patients who have already used the flour, the flour adopts wheat flour as the base material and added with defatted soya vegetable protein powder and dietary fiber powder isolated from soybean tissues, wherein the content of protein is 22 wt %, the content of dietary fiber is 6 wt %, the content of carbohydrate is 65 wt %, and the content of fat is 4 wt % or less based on dry basis of the flour; (4) for patients whose blood glucose level and blood lipid level have returned to normal, whose conditions are not so serious or who have a normal blood lipid level and need to use a small amount of hypoglycemic drugs for maintaining stable blood glucose level, the flour adopts wheat flour as the base material and added with defatted soya vegetable protein powder and dietary fiber powder isolated from soybean tissues, wherein the content of protein is 20 wt %, the content of dietary fiber is 10 wt %, the content of carbohydrate is 65 wt %, and the content of fat is 4 wt % or less based on dry basis of the flour. The above flours were prepared by the production method 1 of the production example.

Comparative Flour 1: the flour uses wheat flour as a base material, and added with defatted soya vegetable protein powder and dietary fiber powder isolated from soybean tissues, wherein the protein content is 23 wt % on a dry basis, the carbohydrate content is 65 wt %, and the fat content is 4 wt % or less based on dry basis of the flour. The dietary fiber powder isolated from soybean tissues was used, and its content is 3 wt %. The production method of this flour is the same as that of the specialized flour of the present invention as described above.

Method: the above flours were used to make foods such as steamed buns and noodles, etc., the type II diabetic patients who have started to use hypoglycemic agents were randomly selected. The total energy for maintaining an ideal body weight were calculated based on age, height, body weight, exercises and labor intensity. For example: (1) for patients who are in the use of hypoglycemic drugs, for example, for inhibiting carbohydrate absorption, promoting the peripheral metabolism of blood glucose, and inhibiting gluconeogenesis, the protein accounted for 20% or the average intake amount of protein is 1.4 g per kilogram of body weight daily; the fat accounts for 20% or less, wherein the saturated fat accounts for 7% or less; the total carbohydrates including starch account for 55%-60%, the amounts range plus or minus 10%. Other nutrients are supplemented according to the general requirements; (2) for patients who are in the use of hypoglycemic drugs, for example, for promoting insulin secretion and sensitizing insulin, or are in the use of insulin directly, the protein accounted for 20% or the average intake amount of protein is 1.2 g per kilogram of body weight daily; the fat accounts for 20% or less, wherein the saturated fat accounts for 7% or less; the total carbohydrates including starch account for 55%-60%, the amounts range plus or minus 10%. Other nutrients were supplemented according to the general requirements; during the experiment, the nutritional management goal can be achieved by adding with other foods such as eggs, milk, lean meat, fish, oats and all kinds of vegetables according to the patient's habits. The type of the hypoglycemic drugs used by the patients was not changed during the experiment, only the dosage of the hypoglycemic drugs was adjusted according to the change of blood glucose levels. The experiment lasted 12 weeks.

Results: the specialized flour of the present invention comprising 23 wt % of protein on a dry basis, 60 wt % of carbohydrates, 4 wt % of fat and 8 wt % of dietary fibers saves 46.1% of the hypoglycemic agents. The Comparative Flour 1 saves 44.9% of the hypoglycemic agents, there is no significant difference (p>0.05). In patients who use the specialized flour of the present invention which is optimized and grouped by nutritional compositions, 50.89% of which stop taking the hypoglycemic agents as the blood glucose level returns to a normal level. Other patients save 55.35% of the hypoglycemic agents, and the total saving rate for the hypoglycemic agents was 78.1%, which is significantly improved when compared with the other two groups (p<0.01).

Remarks: (1) the specialized flour of the present invention can improve the quality of the nutritional management and save the hypoglycemic agents; (2) under the same nutritional management goal, the specialized flour of the present invention optimizes nutritional compositions, thereby facilitating the patients who have or do not have experience in adjusting the hypoglycemic agents to manage the nutrition in combination with the types of the hypoglycemic agents, living habits and foods, such nutrition management is more flexible and personal, and the saving effect of hypoglycemic agents is better; (3) although the saving effect of hypoglycemic agents by the dietary management is related to the reduction of postprandial blood glucose, because the metabolic disorders are corrected, it creates conditions for the patients whose pancreatic islands still can secrete the insulin to reuse their pancreatic islands, Type II diabetes is mainly caused by obesity or increased fat metabolism due to skipping breakfast despite not fat. The formation mechanism of diabetes is not direct islet dysfunction, but the metabolic pathway which lets the blood glucose get into cells is blocked, therefore, the insulin can only act as messengers on the cell surface to transport blood glucose, not play a normal hypoglycemic effect. Therefore, to realize the nutritional management goal characterized by that the saturated fat is significantly lower, the protein is slightly higher and the carbohydrate (saccharide) is slightly lower compared with normal human beings as described in the book *Medical Nutrition Therapy Guidelines for People with Diabetes Mellitus,* that is, on the one hand, the saturated fat needs to be stored should be reduced, on the other hand, the saturated fat needs to be used for maintaining the life should be reduced, thus, the fat passing through the cells, blood or blood vessels will be reduced. The islet function for most type II diabetic patients is always normal. The islet function for other types of diabetic patients is not completely damaged. Therefore, the pancreatic island can work again, The hypoglycemic agents can be reduced or ceased. Meanwhile, the risk factors which are related to cerebrovascular complications such as hyperlipidemia and the like can be prevented and reversed. On the contrary, although the hypoglycemic agents give additional capacity to human body, they cannot get rid of pathogeny and also cannot avoid different production capacity of the carbohydrates from different pathways of hypoglycemic agents, thereby increasing the metabolic disorders, and they becomes a part of the causes and risk factors of complications.

The invention claimed is:
1. A flour composition consisting of a physical mixture of:
superfine refined wheat flour;
rice flour;
defatted soya protein isolate powder; and
dietary fiber powder isolated from soybean tissues, wherein a content of protein is 20-26 wt %, a content of carbohydrate is 65 wt % or less, and a content of fat is 4 wt % or less, each based on dry basis of the flour composition, and wherein the dietary fiber powder isolated from soybean tissues is 410 wt % of the flour composition.

2. The flour composition of claim 1, wherein the superfine refined wheat flour comprises 10.3% of protein, 74.6% of starch, 1.1% of fat, 0.6% of dietary fiber and 12.7% of water;

the rice flour comprises 7.8% of protein, 77.8% of starch, 0.8% of fat, 0.6% of dietary fiber and 12.9% of water;

the defatted soya protein isolated powder comprises 92.1% of protein, 0.8% of fat, 0.8% of dietary fiber and 5.9% of water; and the dietary fiber powder isolated from soybean tissues comprises 20% of protein, 71% of dietary fiber, 1.6% of fat, 1.2% of starch and 5.9% of water.

* * * * *